(12) United States Patent
Arber et al.

(10) Patent No.: US 7,994,306 B2
(45) Date of Patent: Aug. 9, 2011

(54) METHODS OF TREATING CANCER USING SIRNA MOLECULES DIRECTED AGAINST CD24

(75) Inventors: Nadir Arber, Tel-Aviv (IL); Eyal Sagiv, Tel-Aviv (IL)

(73) Assignee: The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 0 days.

(21) Appl. No.: 12/312,487

(22) PCT Filed: Nov. 13, 2007

(86) PCT No.: PCT/IL2007/001396
§ 371 (c)(1),
(2), (4) Date: Jan. 21, 2010

(87) PCT Pub. No.: WO2008/059491
PCT Pub. Date: May 22, 2008

(65) Prior Publication Data
US 2010/0130587 A1 May 27, 2010

Related U.S. Application Data

(60) Provisional application No. 60/858,373, filed on Nov. 13, 2006.

(51) Int. Cl.
*C07H 21/04* (2006.01)
*A61K 31/70* (2006.01)

(52) U.S. Cl. ......................................... 536/24.5; 514/44

(58) Field of Classification Search ........................ None
See application file for complete search history.

(56) References Cited

U.S. PATENT DOCUMENTS

| 2003/0106084 A1* | 6/2003 | Liu et al. .......................... 800/18 |
| 2004/0097448 A1 | 5/2004 | Watt |
| 2005/0245475 A1* | 11/2005 | Khvorova et al. .............. 514/44 |

FOREIGN PATENT DOCUMENTS

| WO | WO 03/079982 | 10/2003 |
| WO | WO 2008/059491 | 5/2008 |

OTHER PUBLICATIONS

Communication Pursuant to Article 94(3) EPC Dated Jan. 27, 2010 From the European Patent Office Re.: Application No. 07827369.5.
International Preliminary Report on Patentability Dated May 28, 2009 From the International Bureau of WIPO Re.: Application No. PCT/IL2007/001396.
International Search Report and the Written Opinion Dated Feb. 27, 2008 From the International Searching Authority Re.: Application No. PCT/IL2007/001396.
Sagiv et al. "CD24 Is A Novel Oncogene in Corectal Cancer, Detected by Microarray Profiling of Cell Transformation, and Is A Target for Immunotherapy of Cancer", Gastroenterology, 130(4, Suppl.2): A680: W1549, 2006. Digestive Disease Week Meeting/107th Annual Meeting of the American-Gastroenterological-Association, Los Angeles, CA, USA, May 2006.
Smith et al. "The Metastasis-Associated Gene CD24 Is Regulated by Ral GTPase and Is A Mediator of Cell Proliferation and Survival in Human Cancer", Cancer Research, 66(4): 1917-1922, 2006. p. 1922, 1-h Col.
Response Dated May 23, 2010 to Communication Pursuant to Article 94(3) EPC of Jan. 27, 2010 From the European Patent Office Re.: Application No. 07827369.5.

\* cited by examiner

*Primary Examiner* — Tracy Vivlemore

(57) ABSTRACT

A method of treating a CD24-related medical condition is disclosed. The method comprises administering to a subject in need thereof at least one siRNA molecule selected from the group consisting of SEQ ID NO: 1 to 4. Pharmaceutical compositions comprising same are also disclosed.

7 Claims, 15 Drawing Sheets

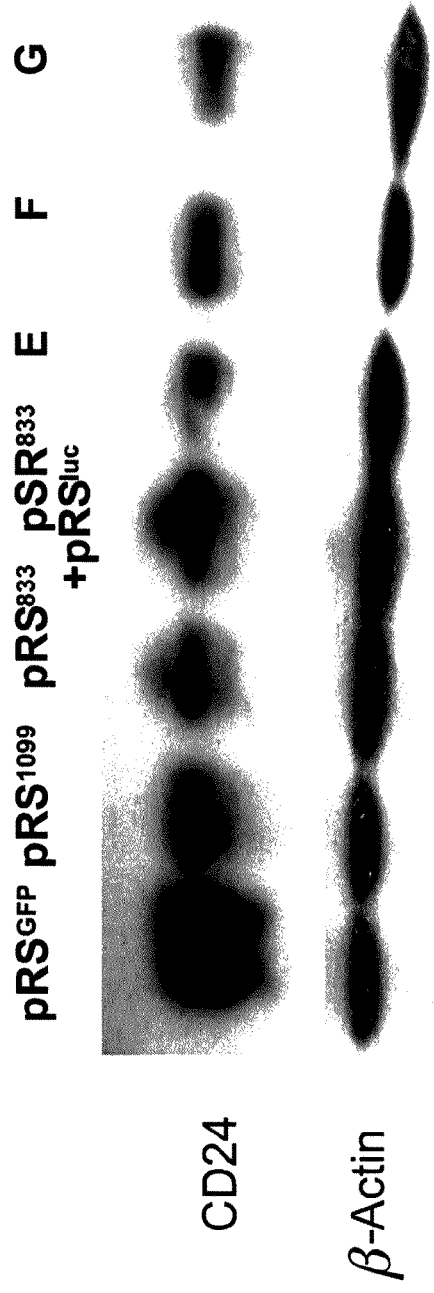
Fig. 3a
Fig. 3b

| E. Variable | GFP | 833(4) | E | G |
|---|---|---|---|---|
| G0/G1 phase (%) | 52.55 ±0.47 | 45.17 ±5.47 | 50.66 ±0.04 | 46.21 ±4.96 |
| S phase (%) | 15.47 ±0.01 | 18.2 ±1.48 | 16.53 ±0.88 | 17.36 ±2.38 |
| G2/M phase (%) | 25.63 ±0.13 | 28.21 ±1.48 | 25.53 ±0.16 | 28.2 ±2.35 |
| Apoptosis (%)* | 3.44 ±0.14 | 4.91 ±1.41 | 4.39 ±0.61 | 4.91 ±0.18 |

```
                          SEQUENCE LISTING

<160> NUMBER OF SEQ ID NOS: 5

<210> SEQ ID NO 1
<211> LENGTH: 19
<212> TYPE: DNA
<213> ORGANISM: Artificial sequence
<220> FEATURE:
<223> OTHER INFORMATION: CD24 RNA interference target sequence

<400> SEQUENCE: 1
tgcatctcta ctcttaaga                                                  19

<210> SEQ ID NO 2
<211> LENGTH: 19
<212> TYPE: DNA
<213> ORGANISM: Artificial sequence
<220> FEATURE:
<223> OTHER INFORMATION: CD24 RNA interference target sequence

<400> SEQUENCE: 2
gctaaacgga ttccaaaga                                                  19

<210> SEQ ID NO 3
<211> LENGTH: 19
<212> TYPE: DNA
<213> ORGANISM: Artificial sequence
<220> FEATURE:
<223> OTHER INFORMATION: CD24 RNA interference target sequence

<400> SEQUENCE: 3
tgtttacatt gttgagcta                                                  19

<210> SEQ ID NO 4
<211> LENGTH: 19
<212> TYPE: DNA
<213> ORGANISM: Artificial sequence
<220> FEATURE:
<223> OTHER INFORMATION: CD24 RNA interference target sequence

<400> SEQUENCE: 4
ttgcattgac cacgactaa                                                  19

<210> SEQ ID NO 5
<211> LENGTH: 1811
<212> TYPE: DNA
<213> ORGANISM: Homo sapiens

<400> SEQUENCE: 5
cggttctcca agcacccagc atcctgctag acgcgccgcg caccgacgga ggggacatgg      60
gcagagcaat ggtggccagg ctcgggctgg ggctgctgct gctggcactg ctcctaccca     120
cgcagattta ttccagtgaa acaacaactg gaacttcaag taactcctcc cagagtactt     180
ccaactctgg gttggcccca atccaacta atgccaccac caaggcggct ggtggtgccc      240
tgcagtcaac agccagtctc ttcgtggtct cactctctct tctgcatctc tactcttaag     300
agactcaggc caagaaacgt cttctaaatt tccccatctt ctaaacccaa tccaaatggc     360
gtctggaagt ccaatgtggc aaggaaaaac aggtcttcat cgaatctact aattccacac     420
```

```
ctttttattga cacagaaaat gttgagaatc ccaaatttga ttgatttgaa gaacatgtga    480
gaggtttgac tagatgatgg atgccaatat taaatctgct ggagtttcat gtacaagatg    540
aaggagaggc aacatccaaa atagttaaga catgatttcc ttgaatgtgg cttgagaaat    600
atggacactt aatactacct tgaaaataag aatagaaata aaggatggga ttgtggaatg    660
gagattcagt tttcatttgg tgcttaattc tataagcgta taaacaggta atataaaaag    720
cttccatgat tctatttata tgtacatgag aaggaacttc caggtgttac tgtaattcct    780
caacgtattg tttcgacggc actaatttaa tgccgatata ctctagatga agttttacat    840
tgttgagcta ttgctgttct cttgggaact gaactcactt tcctcctgag gctttggatt    900
tgacattgca tttgaccttt tatgtagtaa ttgacatgtg ccagggcaat gatgaatgag    960
aatctacccc agatccaagc atcctgagca actcttgatt atccatattg agtcaaatgg   1020
taggcatttc ctatcacctg tttccattca acaagagcac tacattcatt tagctaaacg   1080
gattccaaag agtagaattg cattgaccac gactaatttc aaaatgcttt ttattattat   1140
tattttttag acagtctcac tttgtcgccc aggccggagt gcagtggtgc gatctcagat   1200
cagtgtacca tttgcctccc gggctcaagc gattctcctg cctcagcctc ccaagtagct   1260
gggattacag gcacctgcca ccatgcccgg ctaattttg taattttagt agagacaggg    1320
tttcaccatg ttgcccaggc tggtttcgaa ctcctgacct caggtgatcc acccgcctcg   1380
gcctcccaaa gtgctgggat tacaggcttg agccccgcg cccagccatc aaaatgcttt    1440
ttatttctgc atatgtttga atacttttta caatttaaaa aaatgatctg ttttgaaggc   1500
aaaattgcaa atcttgaaat taagaaggca aaatgtaaag gagtcaaact ataaatcaag   1560
tatttgggaa gtgaagactg gaagctaatt tgcataaatt cacaaacttt tatactcttt   1620
ctgtatatac attttttttc tttaaaaaac aactatggat cagaatagcc acatttagaa   1680
cactttttgt tatcagtcaa tatttttaga tagttagaac ctggtcctaa gcctaaaagt   1740
gggcttgatt ctgcagtaaa tcttttacaa ctgcctcgac acacataaac cttttaaaa    1800 atagacactc c                                                        1811
```

METHODS OF TREATING CANCER USING SIRNA MOLECULES DIRECTED AGAINST CD24

RELATED APPLICATIONS

This application is a National Phase of PCT Patent Application No. PCT/IL2007/001396 having International filing date of Nov. 13, 2007, which claims the benefit of U.S. Provisional Patent Application No. 60/858,373 filed on Nov. 13, 2006. The contents of the above Applications are all incorporated herein by reference.

FIELD AND BACKGROUND OF THE INVENTION

The present invention, in some embodiments thereof, relates to siRNAs capable of down-regulating CD24 and to uses thereof for the treatment of a variety of diseases including cancer.

Cell adhesion proteins are dynamic molecules involved in several aspects of cellular function including migration, inflammation and tissue development. For example, the maturation of hematopoietic cells is associated with the regulated expression of numerous genes, some of which encode cell surface proteins that mediate maturation-stage-specific signals into and out of the cell. This is accomplished by binding of the cell surface protein to a variety of ligands such as soluble interleukins and adhesion receptors either on other cells or within the extracellular matrix. One such cell adhesion molecule found in most cells of hematopoietic lineages is CD24, a glycoprotein consisting of 31 to 35 amino acid residues anchored to the plasma membrane by glycosyl phosphatidylinositol [Kay et al., J. Immunol., 1991, 147, 1412-1416]. The apparent molecular weight of CD24 ranges between 32 KDa in brain and 70 KDa in lymphoid cells due to variable glycosylation patterns. In non-malignant cells CD24 is primarily found in developing (immature but not mature) B-cells and neurons. It has also been detected in cells having a malignant phenotype including neuroblastoma cells [Kadmon et al., Biochem. Biophys. Res. Commun., 1995, 214, 94-101] and malignant brain cells [Poncet et al., Acta. Neuropathol., 1996, 91, 400-408].

The human CD24 gene was cloned by Kay, Rosten and Humphries [Kay et al., J. Immunol., 1991, 147, 1412-1416] and is also disclosed and claimed in PCT publication WO 99/41376 [Yang et al., 1999].

Human CD24 is located on chromosome 6 at band q21. The chromosome region 6q16-q22 has been shown to be associated with recurrent chromosome abnormalities in lymphoproliferative and myeloproliferative diseases [Sandberg, Chromosomes in Human Cancer and Leukemia 2nd ed., 1990, Elsevier: New York, 625-751]. Additional homologous sequences of CD24 have been mapped to chromosomes 15q21-q22 and Yq11. CD24 is thus a member of a multigene family but it is not known yet known if the genes related to CD24 are functional (Hough et al., Genomics, 1994, 22, 154-161). Pass et al have shown that the 5'-flanking sequence of CD24 has cell-type-specific activity resulting in enhancement of expression of CD24 (relative to a control promotor) in small cell lung cancer cell lines [Pass et al., Int. J. Cancer, 1998, 78, 496-502].

The principal cellular function of human CD24 is not clear but several B cell-related functions have been suggested. CD24 is involved in B cell adhesion both directly and by modifying the specificity and/or avidity of other adhesive interactions such as the interactions between VLA-4 and VCAM-1, VLA-4 and fibronectin [Hahne et al., J. Exp. Med., 1994, 179, 1391-1395] and the interaction of VLA-5 with L1 [Ruppert et al., J. Cell Biol., 1995, 131, 1881-1891]. The investigations of Zarn et al. indicate an involvement of CD24 in the signaling processes of kinases c-fgr in small cell lung cancer and with kinase lyn in erythroleukemia [Zarn et al., Biochem. Biophys. Res. Commun., 1996, 225, 384-391].

Studies of the interactions of CD24 with P-selectin in a breast cancer carcinoma cell line indicate that CD24 may play a role in mediating an adhesion pathway in cancer metastasis [Aigner et al., Faseb. J., 1998, 12, 1241-1251].

In a rat glioma cell line, it was found that CD24 stimulates the migration of gliomas. This suggests a role for CD24 in promotion of brain invasion by human gliomas [Senner et al., J. Neuropathol. Exp. Neurol., 1999, 58, 795-802].

Anti-CD24 antibodies (in some cases including immunotoxins) have been used to inhibit CD24 in investigative and therapeutic efforts to control various diseases including: Epstein-Barr virus-induced B-lymphoproliferative disorder, [Benkerrou et al., Blood, 1998, 92, 3137-3147; Fischer et al., N. Engl. J. Med., 1991, 324, 1451-1456; Lazarovits et al., Clin. Invest. Med., 1994, 17, 621-625], small cell lung cancer [Jackson et al., Cancer Res., 1992, 52, 5264-5270; Zangemeister-Wittke et al., Int. J. Cancer, 1993, 53, 521-528; Zarn et al., Biochem. Biophys. Res. Commun., 1996, 225, 384-39] and Burkitt's lymphoma [Schnell et al., Int. J. Cancer, 1996, 66, 526-531].

U.S. Pat. Appl. 20040097448 teaches therapeutic strategies aimed at inhibiting the action of CD24 by administering anti sense oligonucleotides targeted to nucleic acid encoding CD24 for the treatment of small cell lung cancer and breast cancer (as well as other pathologies including autoimmune neurologic diseases, blood disorders and conditions related to excessive apoptosis).

Smith et al [Cancer Research 66, 1917-1922, Feb. 15, 2006] teaches that down-regulation of CD24 using siRNAs in a panel of tumor cell lines (from common epithelial human cancers, including UM-UC-3 urothelial carcinoma cells, DU145 prostate carcinoma cells, HeLa cervical adenocarcinoma cells, MCF-7 breast adenocarcinoma, and SAOS-2 osteosarcoma cells) leads to a decrease in cellular proliferation.

U.S. Pat. Appl. 20040005596 teaches administration of siRNA molecules targeted to CD24 for the treatment of a variety of cancers.

SUMMARY OF THE INVENTION

According to an aspect of some embodiments of the present invention there is provided a method of treating a CD24-related medical condition, the method comprising administering to a subject in need thereof at least one siRNA molecule selected from the group consisting of SEQ ID NO: 1 to 4, thereby treating the CD24-related medical condition.

According to an aspect of some embodiments of the present invention there is provided an siRNA molecule selected from the group consisting of SEQ ID NO: 1-4.

According to an aspect of some embodiments of the present invention there is provided an article of manufacture comprising two siRNA molecules set forth by SEQ ID NOs: 3 and 4.

According to an aspect of some embodiments of the present invention there is provided a pharmaceutical composition comprising at least one siRNA molecule, wherein the siRNA molecule is selected from the group consisting of SEQ ID NO: 1-4.

According to an aspect of some embodiments of the present invention there is provided a use of at least one siRNA molecule selected from the group consisting of SEQ ID NO: 1-4, for the manufacture of a medicament identified for treating a CD24-related medical condition.

According to some embodiments of the invention, the CD24-related medical condition is selected from the group consisting of a hyperproliferative disease and an autoimmune disease.

According to some embodiments of the invention, the hyperproliferative disease is a colorectal cancer.

According to some embodiments of the invention, the at least one siRNA molecule is two siRNA molecules set forth by SEQ ID NOs: 3 and 4.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A-E are photographs and graphs illustrating the level of CD24 expression in HT29 cells following expression of two siRNAs to CD24 in a single clone. FIG. 3A: CD24 mRNA levels shown via semi-quantitive RT-PCR with CD24 specific primers. The house keeping gene GAPDH served as the control for equal loading. FIG. 3B: Western blot analysis for CD24 expression, loading 20 μg of total lysate from each clone onto an SDS-PAGE. Membranes were incubated with a 1:500 dilution of SWA11 antibodies. β-Actin expression was used for normalization. FIG. 3C: Western blot analysis for the indicated Colo357 clones of pRS$^{833}$ and controls performed similarly (loading 50 μg protein). FIGS. 3D-E: Flow cytometry analysis of cells incubated with anti-CD24 ML5 antibodies and FL-conjugated anti-mouse secondary antibodies was used to assess the CD24 expression levels on the membrane; the final CD24 levels were thus define as the mean.

FIGS. 4A-E are graphs and table illustrating that down-regulation of CD24 slows cell growth: FIGS. 4A and 4C: HT29 cells and the siRNA control cells (GFP), and clones 833(4), E, and G were plated in triplicates in twelve-well plates in complete medium (FIG. 4A) or starvation-0.5% FBS (FIG. 4C). Number of cells was determined every 2-3 days using a Coulter counter. FIGS. 4B and 4D: Colo357, its clones 833 (4, 10 and 12) and their controls were similarly examined. Each experiment was repeated at least twice. FIG. 4E: Cell cycle parameters for exponentially growing HT29 and its discussed clones following PI staining for DNA content.

FIG. 6A: 6*$10^4$ cells per well of HT29 cells and their CD24 under-expressing derivatives were seeded onto the upper chamber of a transwell plate (0.8 μm pore-size, Corning, N.Y.). 48 hours later, cells were fixated to the plate using PFA and stained in crystal violet. Picture was taken after wiping off the cells from the upper chamber using a cotton-stick. FIG. 6B: The number of cells was determined using the TINA2.0 software by reading the mean color intensity per well. The experiment was performed twice in duplicates; results are presented in percents compared to the control clone for each experiment.

DESCRIPTION OF EMBODIMENTS OF THE INVENTION

The present invention, in some embodiments thereof, relates to siRNAs capable of down-regulating CD24 and use thereof in treating medical conditions such as cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

CD24 expression has been correlated with a wide variety of diseases including hyperproliferative disorders such as cancer and autoimmune diseases. Moreover, down-regulation of CD24 has been postulated as a means of treating such diseases. The present inventors have uncovered four different siRNAs which are capable of down-regulating CD24 and have proven therapeutic efficacy of such molecules in both in vitro and in vivo colorectal cancer models.

Whilst reducing the present invention into practice, the present inventors have shown that the siRNAs of the present invention are capable of decreasing proliferation and migration of cells derived from human colorectal carcinoma (FIG. 7). Furthermore, injection of such cells expressing at least one of the siRNAs of the present invention into nude mice result in slower tumor formation as compared to control cells not expressing the siRNAs of the present invention (FIG. 6).

Figure 5A:
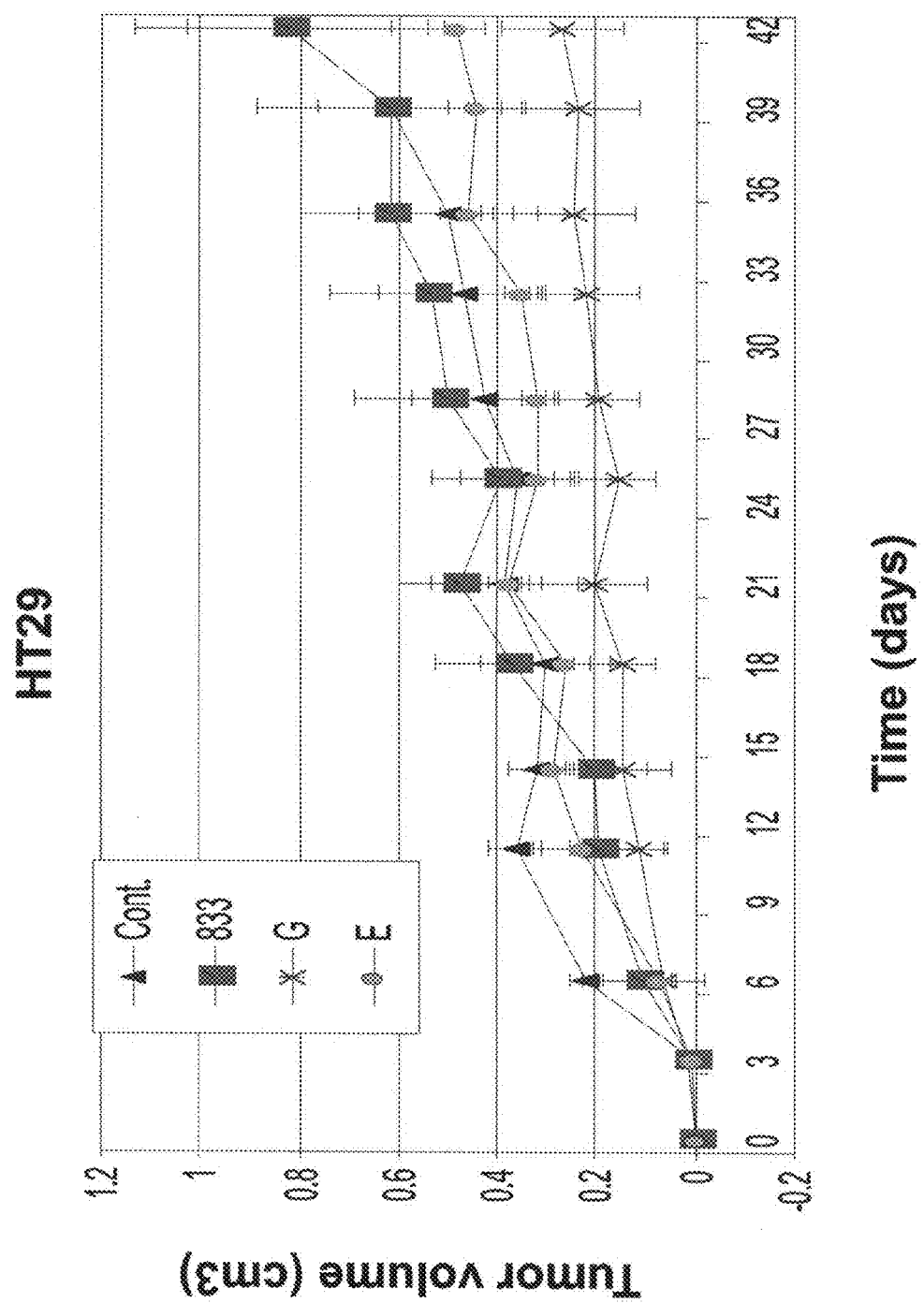
FIGS. 5A-B are graphs illustrating that CD24 down-regulation results in lowered tumorigenicity: HT29 (FIG. 5A) and Colo357 (FIG. 5B) cells and their CD24 under-expressing clones were injected subcutaneously into each of two flanks of athymic nude mice (5-7*$10^6$ cells per injection, 5 mice per group). Tumor volumes were measured twice weekly standard error bars are presented for each measurement.
Figure 5B:
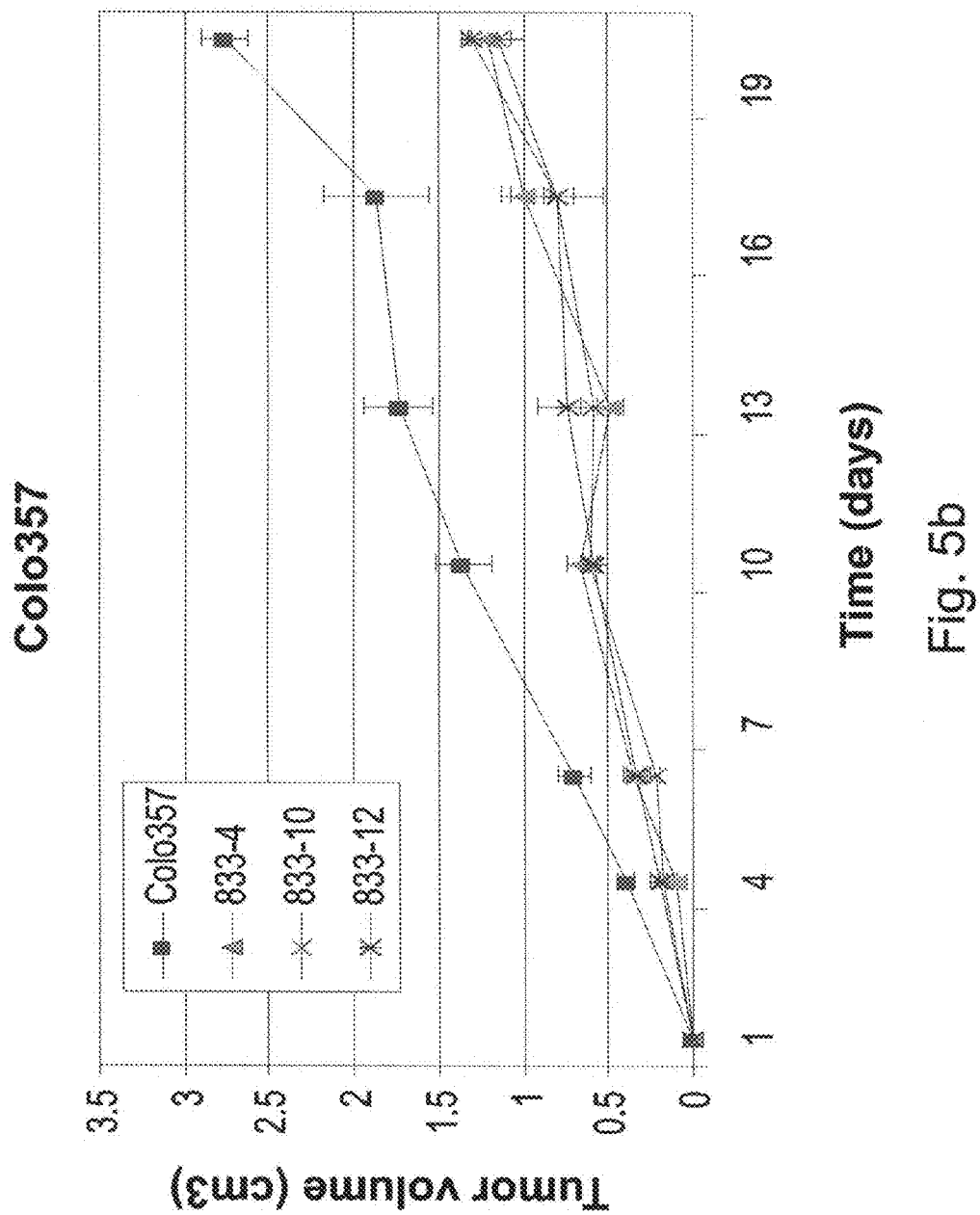

In addition, the present inventors have shown that a combination of two of the siRNAs of the present invention (SEQ ID NOs: 3 and 4) are particularly effective at reducing CD24 expression (FIGS. 3 and 5B). Accordingly, a combination of the above mentioned siRNAs were able to decrease CD24 expression by more than 90%.

Thus, according to one aspect of the present invention there is provided a method of treating a CD24-related medical condition. The method comprises administering to a subject in need thereof at least one siRNA molecule selected from the group consisting of SEQ ID NO: 1 to 4.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The phrase "CD24-related medical condition" as used herein, refers to a disease or disorder that results from an expression of CD24. Exemplary CD24-related medical conditions include, but are not limited to hyperproliferative disorders such as cancer (e.g. colorectal cancer) and autoimmune diseases which are further described herein below.

As used herein, the phrase "subject in need thereof" refers to a subject which has the disease, or which is susceptible to having the disease. The subject may be a mammal, e.g. a human. For example if the disease being treated is colorectal cancer, the subject is typically one being diagnosed with colorectal cancer, with or without metastasis, at any stage of the disease (e.g., TX, T0, Tis, T1, T2, T3, T4, NX, N0, N1, MX, M0 and M1).

As mentioned, down-regulating the level of CD24 may be effected by administering to the subject a small interfering RNA (siRNA) molecule.

The term "siRNA" as used herein, refers to small interfering RNAs, which also include short hairpin RNA (shRNA) [Paddison et al., Genes & Dev. 16: 948-958, 2002], that are capable of causing interference and can cause post-transcriptional silencing of specific genes in cells, for example, mammalian cells (including human cells) and in the body, for example, mammalian bodies (including humans).

RNA interference is a two step process. The first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 by duplexes (siRNA), each with 2-nucleotide 3' overhangs [Hutvagner and Zamore Curr Opin Genetics and Development 12:225-232 (2002); and Bernstein, Nature 409:363-366 (2001)].

In the effector step, the siRNA duplexes bind to a nuclease complex from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr Op Gen Develop. 12:225-232 (2002); Hammond et al., 2001. Nat Rev Gen. 2:110-119 (2001); and Sharp Genes Dev. 15:485-90 (2001)]. Although the mechanism of cleavage is still to be elucidated, research indicates that each RISC contains a single siRNA and an RNase [Hutvagner and Zamore, Curr Opin Gen. Develop. 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al., Nat Rev Gen. 2:110-119 (2001), Sharp Genes Dev. 15:485-90 (2001); Hutvagner and Zamore Curr Opin Gen. Develop. 12:225-232 (2002)]. Ample guidance for using RNAi to practice the present invention is provided in the literature of the art [refer, for example, to: Tuschl, ChemBiochem. 2:239-245 (2001); Cullen, Nat Immunol. 3:597-599 (2002); and Brantl, Biochem Biophys Acta 1575:15-25 (2002)].

Synthesis of RNAi molecules suitable for use with the present invention can be effected as follows. First, the mRNA sequence encoding the polypeptide of the present invention is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs), being enriched in regulatory protein binding sites. UTR-binding proteins and/or translation initiation complexes may interfere with binding of the siRNA endonuclease complex [Tuschl, Chem Biochem. 2:239-245]. It will be appreciated though, that siRNAs directed at untranslated regions may also be effective, as demonstrated for GAPDH wherein siRNA directed at the 5' UTR mediated approximately 90% decrease in cellular GAPDH mRNA and completely abolished protein level (http://www.ambion.com/techlib/tn/142/3.html or http://www.ambion.com/techlib/tn/131/4.html).

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

As is described in the Examples section which follows siRNAs set forth by SEQ ID NOs: 1-4 were shown to be effective at down-regulating levels of CD24.

It will be appreciated that single siRNAs may be used for the treatment of CD24 related diseases or alternatively combinations of the above mentioned siRNA molecules may be used. Such combinations may be packaged together as a single article of manufacture. A particularly effective combination (SEQ ID NOs: 3 and 4) is disclosed in the Examples section herein below wherein a reduction of CD24 greater than 90% is achieved.

Delivery of siRNA and expression constructs/vectors comprising siRNA are known by those skilled in the art. U.S. applications 2004/106567 and 2004/0086884, which are herein incorporated by reference in their entirety, provide numerous expression constructs/vectors as well as delivery mechanism including, but not limited to viral vectors, non viral vectors, liposomal delivery vehicles, plasmid injection systems, artificial viral envelopes and poly-lysine conjugates.

One skilled in the art would understand regulatory sequences useful in expression constructs/vectors with siRNA. For example, regulatory sequences may be a constitutive promoter, an inducible promoter, a tissue-specific promoter, or a combination thereof.

The siRNAs of the present invention may be administered systemically or locally (e.g. intratumoral injection) as further described herein below.

As mentioned, the siRNAs of the present invention may be used to treat diseases such as hyperproliferative diseases and autoimmune diseases.

Types of hyperproliferative diseases amenable to treatment via the method of the present invention include benign tumors, warts, polyps, precancers, and malignant tumors/cancer.

As used herein the term "cancer" refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells.

Specific examples of cancer which can be treated using the siRNAs of the present invention include, but are not limited to, adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, meningioma; multiple endocrine neoplasia; myeloid malignancy, predisposition to; myxosarcoma, neuroblastoma; osteosarcoma; ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

According to one embodiment of this aspect of the present invention, the cancer is colonorectal cancer.

As used herein, the phrase "colorectal cancer" refers to malignant tumors of the epithelium of the colon or rectal, including but not limited to squamous cell (epidermoid) carcinomas, cloacogenic (basaloid transitional cell) tumors, and adenocarcinomas.

Exemplary autoimmune diseases that may be treated with the siRNAs of the present invention include, but are not limited to rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2): 49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol Dec. 15, 2000; 165 (12): 7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol Jan. 1, 2001; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. May 13, 1998; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr Aug. 25, 2000; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. Jun. 17, 1999; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah Jan. 16, 2000; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

The siRNAs of the present invention may be administered per se or as part of a pharmaceutical composition.

As used herein a "pharmaceutical composition" refers to a preparation of one or more of the active ingredients described herein with other chemical components such as physiologically suitable carriers and excipients. The purpose of the pharmaceutical composition is to facilitate administration of the active ingredients to the subject.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered active ingredients. An adjuvant is included under these phrases.

Herein, the term "excipient" refers to an inert substance added to the pharmaceutical composition to further facilitate administration of an active ingredient of the present invention. Examples, without limitation, of excipients include calcium carbonate, calcium phosphate, various sugars and types of starch, cellulose derivatives, gelatin, vegetable oils and polyethylene glycols. The pharmaceutical composition may advantageously take the form of a foam or a gel.

Techniques for formulation and administration of drugs may be found in "Remington's Pharmaceutical Sciences," Mack Publishing Co., Easton, Pa., latest edition, which is incorporated herein by reference.

Suitable routes of administration include any of various suitable systemic and/or local routes of administration.

Suitable routes of administration may, for example, include the inhalation, oral, buccal, rectal, transmucosal, topical, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes; and/or the route of direct injection into a tissue region of the subject.

The pharmaceutical composition may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

For transmucosal administration, penetrants appropriate to the barrier to be permeated are used in the formulation. Such penetrants are generally known in the art.

For oral administration, the pharmaceutical composition can be formulated readily by combining the active ingredients with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration via the inhalation route, the active ingredients for use according to the present invention can be delivered in the form of an aerosol/spray presentation from a pressurized pack or a nebulizer with the use of a suitable propellant, e.g., a fluorochlorohydrocarbon such as dichlorodifluoromethane, trichlorofluoromethane, dichloro-tetrafluoroethane; carbon dioxide; or a volatile hydrocarbon such as butane, propane, isobutane, or mixtures thereof. In the case of a pressurized aerosol, the dosage unit may be determined by providing a valve to deliver a metered amount. Capsules and cartridges of, e.g., gelatin for use in a dispenser may be formulated containing a powder mix of the active ingredients and a suitable powder base such as lactose or starch.

The pharmaceutical composition may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

A pharmaceutical composition for parenteral administration may include an aqueous solution of the active ingredients in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredients may be in powder form for constitution with a suitable vehicle, e.g., sterile, pyrogen-free water based solution, before use.

The pharmaceutical composition may also be formulated in rectal compositions such as suppositories or retention enemas, using, e.g., conventional suppository bases such as cocoa butter or other glycerides.

The pharmaceutical composition should contain the active ingredients in an amount effective to achieve disease treatment.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredients which are sufficient to achieve the desired therapeutic effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of the composition to be administered will be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredients. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorpotaed by reference as if fully set forth herein. Other general references are provided throughout this document. The procedures therein are believed to be well known in the art and are provided for the convenience of the reader. All the information contained therein is incorporated herein by reference.

Example 1

Analysis of CD24 Expression in CRC

Mutations in oncogenes and tumor suppressor genes, abnormal gene expression and genetic defects are intimately involved in CRC carcinogenesis. Differential gene expression analysis, using microarrays, provides a comprehensive profile of the relative mRNA levels, thus providing new insight into the various biologic pathways involved in disease pathogenesis, progression, and response to therapy. Microarray technology has been applied successfully in the study of many malignancies, including CRC; The present inventors employed expression arrays (utilizing the Affymetrix rat (RG-U34) Genechip®) to characterize altered gene expression in normal and transformed enterocytes. For that purpose, a unique CRC in vitro model was used that consists of a variety of normal and transformed intestinal cell lines. Normal enterocytes derived from rat ileum (IEC 18 cells), were transfected with a variety of oncogenes (Ras, cyclin D1, antisense bak, CENP-C, bcl-2, WNT-2) and became transformed.

It was shown that Ras transformed IEC-18 (R1) cells are most aggressive. With this cell line, out gene expression profiling was effected (using Affymetrix rat (RG-U34) Genechip®) following short (72 hours) and long (6 months) durations of exposure to celecoxib (Pfizer, N.Y., USA), a specific COX-2 inhibitor that is a promising agent in CRC chemoprevention. Gene expression arrays were employed in-order to identify novel target genes with altered gene expression in transformed cells. Of the approximately 20,000 genes present on the Affymetrix chip, 1,081 were differentially expressed (>2-fold) in the R1 cells. Among these, a cluster of 71 genes showed a reversion to normal expression levels following exposure to COX 2 inhibitor, as compared to non-transformed cells. CD24 was among these, identified as being overexpressed in transformed relative to non-transformed enterocytes and revert back to low expression following exposure to celecoxib.

The present example seeks to validate the increased expression of CD24.

Materials and Methods

Immunostaining: 398 biological samples from the entire GI tract (normal, adenomatous polyps and adenocarcinomas) were stained for CD24 using monoclonal anti-CD24 antibodies The immunohistochemical analyses were performed with an avidin-biotin complex immunoperoxidase technique (Umansky et al., 2001). 4 μm tissue sections were mounted on poly-L-lysine coated slides. After deparaffinization in Ameri-clear (Baxter, McGaw Park, Ill.) and absolute ethanol, sections were hydrated through a series of graded alcohol, distilled water, and PBS, at pH 7.4. Slides were then immersed in 10 mM citrate buffer (pH=6) and microwaved at 750 W for a total of 10 minutes. After blocking with goat serum for 20 minutes, the primary antibodies, anti-CD24 MAb (Ab-2, clone 24C02, from Neomarkers, Fremont, Calif.), were applied and incubated overnight at 4° C. in a high-humidity chamber. Although all concentrations of primary antibody gave good membranous staining, the ideal concentration with minimal background was 20 μg/mL. As a negative control, duplicated sections of selected tissue samples were immunostained in the absence of the primary antibody. Subsequent steps utilized the Vectastain rabbit Elite ABC kit (Vector Laboratories, Burlingame, Calif.) according to the manufacturer's instructions. Color development was accomplished with 0.375 mg/dl solution of a 3,3'-diamino-benzidine tetrahydro chloride (Sigma Chemical Co., St. Louis, Mo.) containing 0.0003% hydrogen peroxide. Slides were counterstained with hematoxylin and dehydrated, and cover slips were applied using Acrytol mounting medium (Surgipath Medical Industries, Richmond, Ill.).

Interpretation of IHC Staining: Membrane staining was considered positive if the chromogen was detected in at least 5% of the cells within a microscopic field.

The samples included tissue specimens from normal adjacent mucosa and tumors of the esophagus, stomach, pancreas and small and large bowel. Positive staining represents an intensity score of the membrane/cytoplasm >1 on a scale of 0, 1, 2, and 3 of increasing intensity.

Results

CD24 was shown to be over-expressed in these tumors, both at an early stage of the multi-step carcinogenesis process as well as in later stages of the process, as it was expressed to the same extent in adenomas (the pre-malignant stage of CRC), as well as in carcinomas (Table 1, herein below).

TABLE 1

| CD24 staining | Colon and Rectum | | | Entire GI tract | | |
|---|---|---|---|---|---|---|
| | Normal Tissue | Adenoma | Carcinoma | Normal Tissue | Adenoma | Carcinoma |
| Negative N (%) | 45 (83.3) | 5 (9.2) | 9 (13.6) | 122 (83) | 21 (22.1) | 45 (28.8) |
| Positive N (%) | 9 (16.6) | 49 (90.7) | 57 (86.3) | 25 (17) | 74 (77.9) | 111 (71.2) |
| Total N (%) | 54 (100) | 54 (100) | 66 (100) | 147 (100) | 95 (100) | 156 (100) |

Example 2

Down Regulation of CD24 Expression in Colorectal Cancer cells

Materials and Methods

Construction of plasmids: Four 19 base-pairs sequences were selected from the cDNA sequence of CD24 and the most efficient siRNA molecule comprised of same was saught. The sequences were chosen according to the recommendations of two siRNA design software, available for free access on the websites of the companies Dharmacon and Genscript. Four different plasmids were designed since it was estimated that the odds of success in achieving down regulation with a single siRNA sequence are usually around 1:4. The chosen sequences were named by the position on the cDNA of the first (5') nucleotide (accession number: M58664, NCBI):

```
    283:    TGCATCTCTACTCTTAAGA    (SEQ ID NO: 1)

1074:   GCTAAACGGATTCCAAAGA    (SEQ ID NO: 2)

833:    TGTTTACATTGTTGAGCTA    (SEQ ID NO: 3)

1099:   TTGCATTGACCACGACTAA    (SEQ ID NO: 4)
```

For the construction of stable expression vectors to deliver these molecules, commercially available pSUPER-RNAi System™, OligoEngine™ were used. These are based on the technology of expressing short-hairpin RNA molecules transcribed continuously from a regular double-strand expression vector.

Accordingly, four 64 base-pairs oligos, and their anti-sense, were designed according to the protocol of the pSU-PER-RNAi System™ where the desired sequences for CD24 siRNA were inserted in the specified places in order to reach the sequence that encodes for the shRNA structure. The oligo-sequences were ordered and synthesized (Sigma-Aldrich, Israel). Each oligo and its anti-sense sequence were annealed (10' at 70° C.) and inserted into the pSUPER vectors. Each of the four sequences was inserted to two different vectors: pSUPER-Puro that contains puromycine-resistance gene and a non-commercially available pSUPER-Hygro that contains hygromycine-resistance gene. Altogether 8 vectors were constructed with four different siRNA sequences to CD24 and two different selectable markers.

Additional vectors were prepared to serve as a control to the effect of non-specific shRNA molecules in the cells. Thus the specific effect of CD24 down-regulation could be distinguished from the effect of the transfection, selection and siRNA. Two siRNA sequences, to the non-eukaryotic genes to Luciferase and GFP were inserted each to the pSUPER-Puro and pSUPER-Hygro vectors.

Western blot analysis: Cell lysates (50 µg protein) from human CRC and pancreatic cancer cell lines were analyzed on 10% PAGE for CD24 expression. The blot was probed with mouse anti-CD24 (SWA11) antibodies and then with HRP-labeled anti-mouse antibodies. The membranes were incubated with human anti-CD24 MAb (SWA11) and polyclonal anti-actin (I-19, Santa Cruz, Calif.) antibodies for 1 hour at room temperature. The membranes were washed as described above and incubated with 1:2,000 anti-mouse and anti-goat secondary antibodies respectively (Jackson Laboratories, UK) for 1 hour at room temperature. Additional washes were carried out with PBS-Tween and immune detection was done using the ECL Western blotting detection system (Amersham).

Formation of stable CD24-down-regulated HT29 clones: The formation of stable CD24-down-regulated HT29 clones was effected by two transfections, selection with the respective antibiotics and clonal expansion. During the first step HT29 cells were transfected with the six vectors: pSUPER-Puro-284, pSUPER-Puro-833, pSUPER-Puro-1074 and pSUPER-Puro-1099 to CD24 and pSUPER-Puro-GFP and pSUPER-Puro-Luc (luciferase) as a control.

Cell culture and formation of clones: The human colorectal (HT29) and pancreatic (Colo357) cancer cell lines were obtained from the American Type Culture Collection (Manassas, Va.), cultured in Dulbecco's modified Eagle medium (Sigma, Israel) containing 5%-10% fetal bovine serum (Biological Industries, Beit Haemek, Israel), 1% penicillin, and 1% streptomycin (complete medium) at 37° C. in an atmosphere of 95% oxygen and 5% $CO_2$.

Transfections were performed using LipofectAMINE and Plus Reagents (Invitrogen, Life Technologies, Carlsbad, Calif.) according to the manufacturer's instructions. A total of $7 \times 10^5$ cells were seeded in six-well plates. The next day, 50% confluent dishes were transfected with 1 µg vectors. At first, cells were transfected with $pRS^{833}$, $pRS^{luc.}$ and $Prs^{GFP}$; resistant cells were selected in complete medium with 1 µg/ml puromycin (Sigma, Israel) for three weeks. Following selection, drug-resistant (puro+) clones were isolated from two different plates [designated 833(1)-833(6), GFP(1)-GFP(3) and Luc.(1)-Luc.(3)]. Clone 833(4), which showed the most significant decrease in CD24 expression was expanded and transfected similarly with $pRS^{1099}$ and $pRS^{GFP}$ that have hygromycin as the selectable marker; resistant cells were selected in complete medium with 1 µg/ml puromycin and 450 µg/ml hygromycin (Sigma) for three weeks. Following selection, drug-resistant (puro+/hygro+) clones were isolated [designated 833+1099(A-G), 833+GFP(1-3)]. For confirmation of the results in another cell line, Colo357 were transfected similarly with the vectors $pRS^{833}$, $pRS^{luc.}$ and $pRS^{GFP}$ and puro+ clones were selected and expanded. Four resistant clones were randomly chosen, designated 833-1, 4, 10 and 12. 3-4 clones were expanded from each of the siRNA and 2 from each control vector.

Flow cytometry Analysis: In order to confirm the results from the Western-blot analysis and to more specifically determine the CD24 content on the cell surface, flow cytometry was performed using a fluorescence labelled anti-CD24 monoclonal antibody (ML-5) and secondary fluorescent antimouse antibodies (Jackson Laboratories, UK). Cells were plated at a density of $5 \times 10^6$ per 10 cm dish in complete medium and harvested 72 hours later when they reached ~70% confluency.

Results

Figure 1:
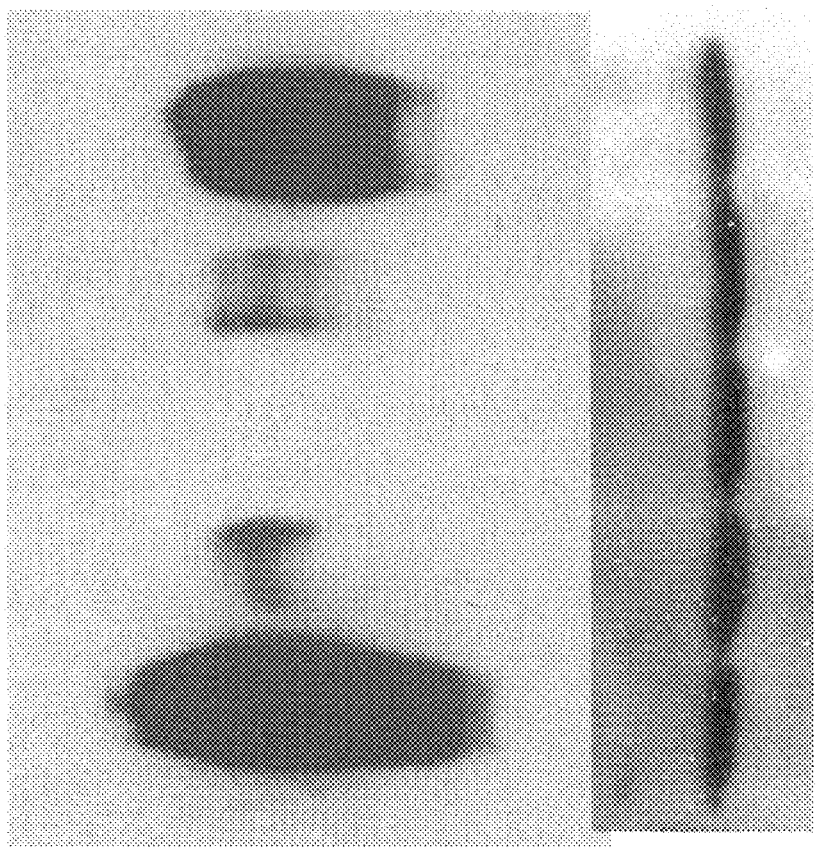
FIG. 1 is a photograph of a Western blot analysis illustrating the level of CD24 expression in various human CRC and pancreatic cancer cell lines as compared to β-actin. HT-29 (lane 1), SW480 (2), HCT116 (3), CaCo2 (4) and Colo320 (5).

As illustrated in FIG. 1, the HT29 cell line, derived from human colorectal carcinoma, was shown to have the strongest endogenous expression of CD24 in Western blot analysis.

Figure 2:
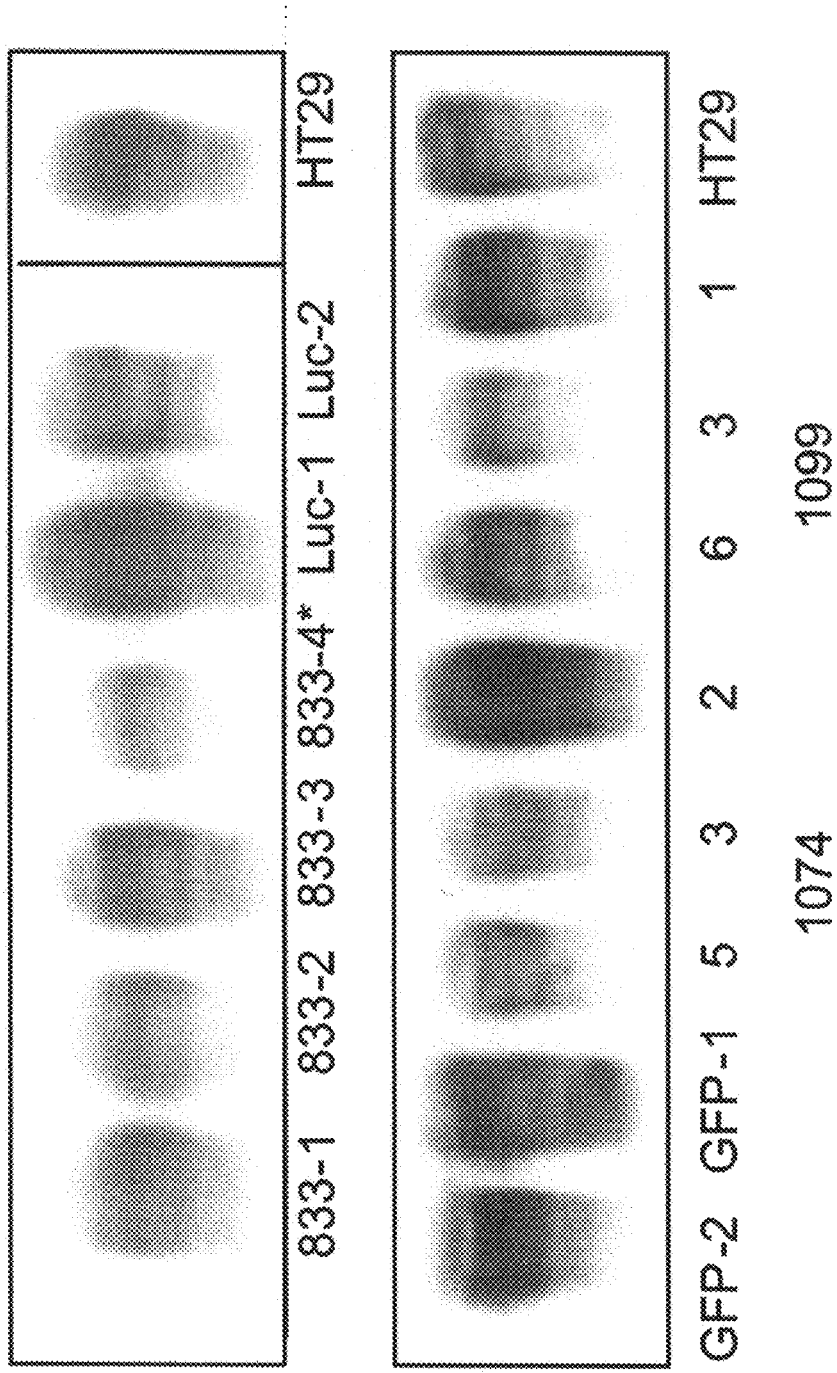
FIG. 2 is a photograph of a Western blot analysis illustrating the level of CD24 expression in HT29 cells following expression of siRNA to CD24 at positions 833 (SEQ ID NO: 3), 1074 (SEQ ID NO: 2) and 1099 (SEQ ID NO: 4) as compared to expression of control siRNA sequences to luciferase and GFP.

As illustrated in FIG. 2, three siRNA sequences (all but 284, data not shown) yielded clones with significant reduction in the CD24 protein.

Figure 3C:
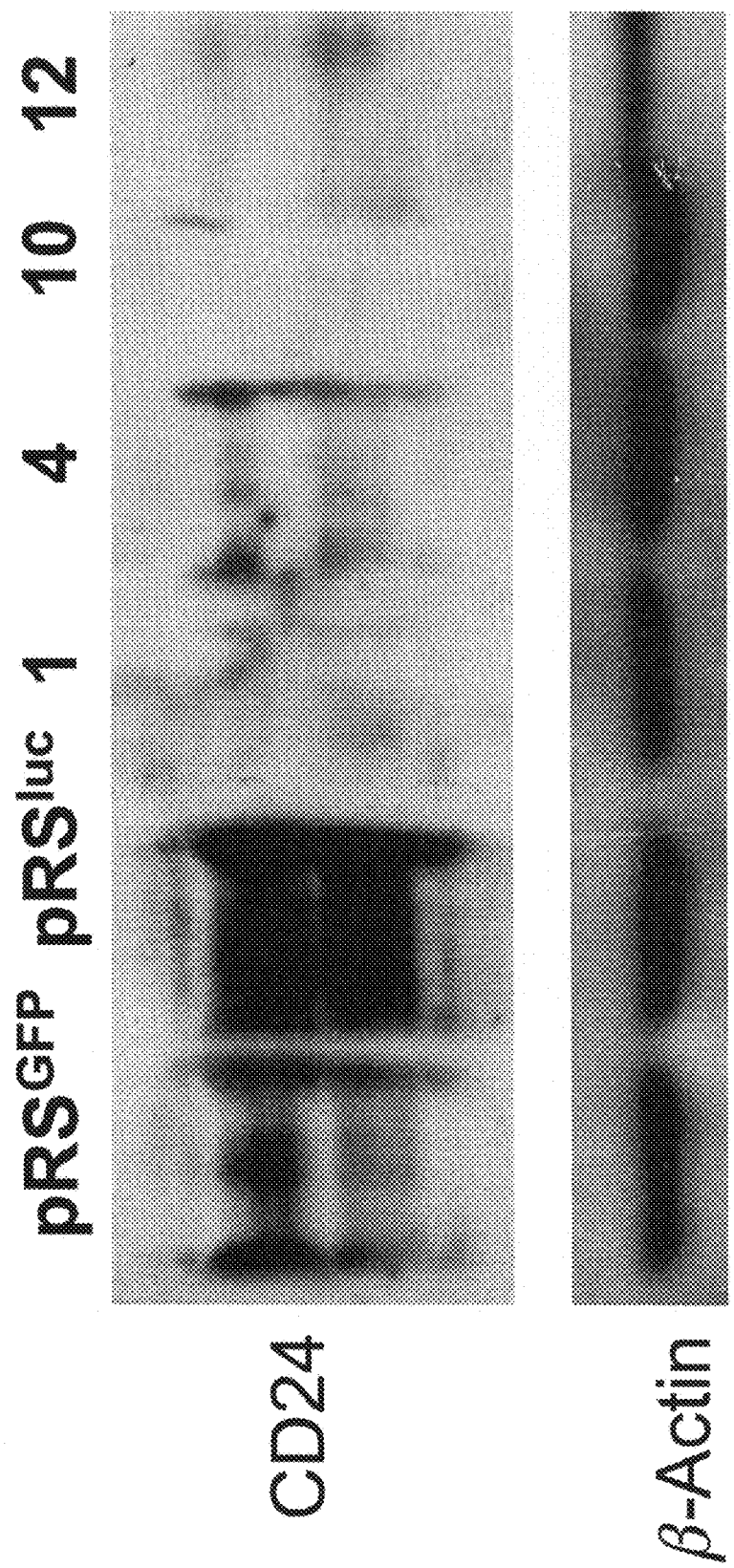
Figure 3D:
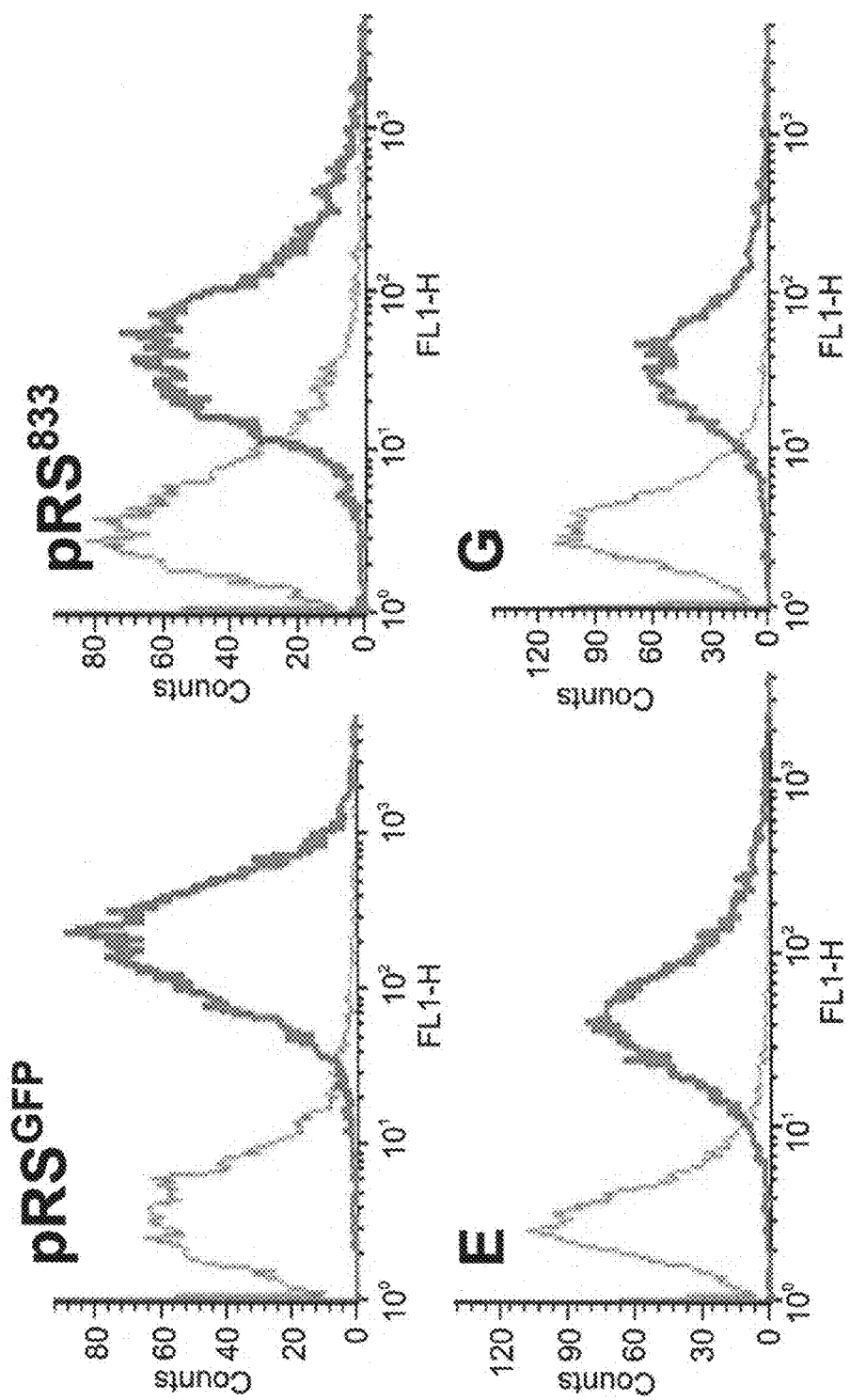
Figure 3E:
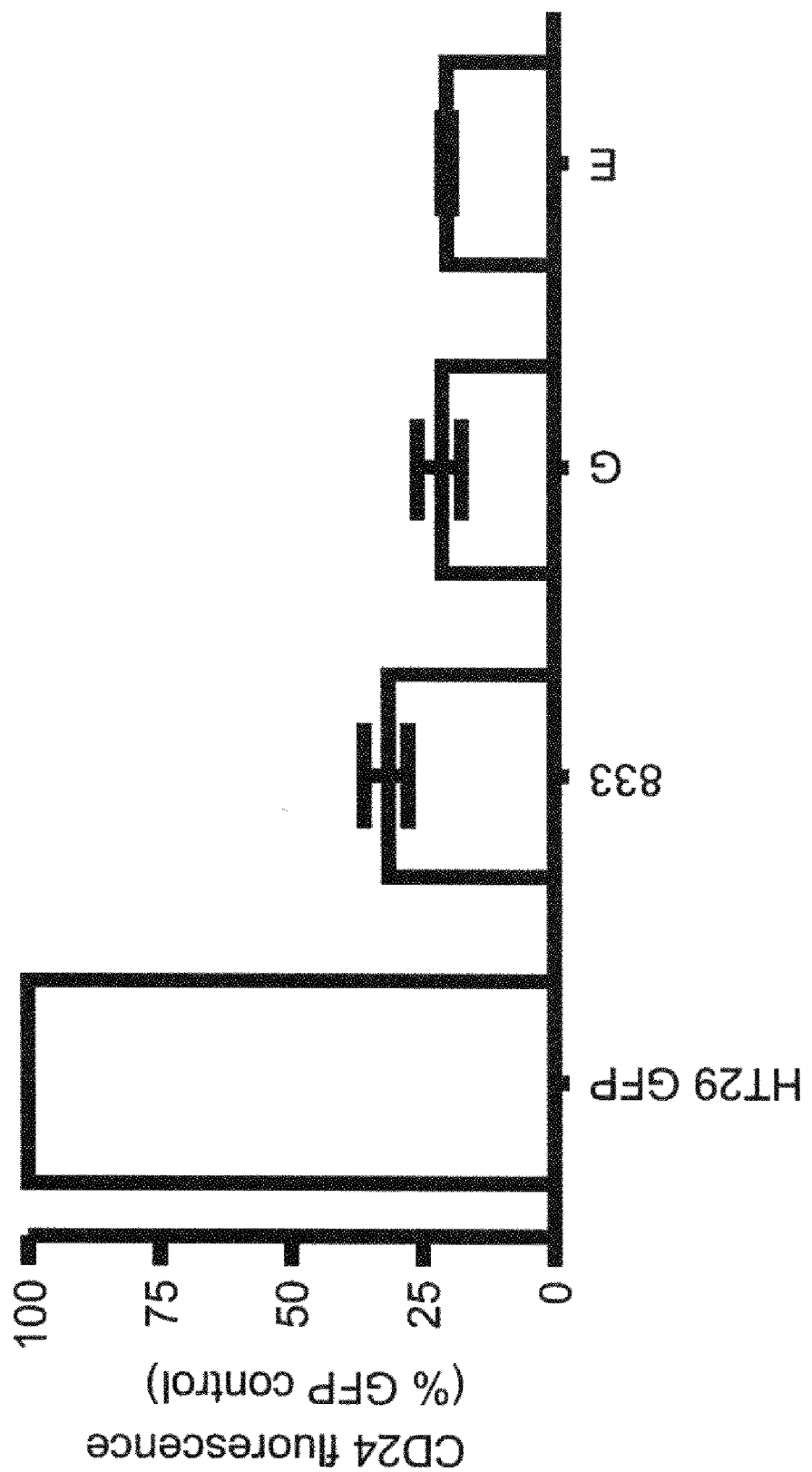
Figure 4A:
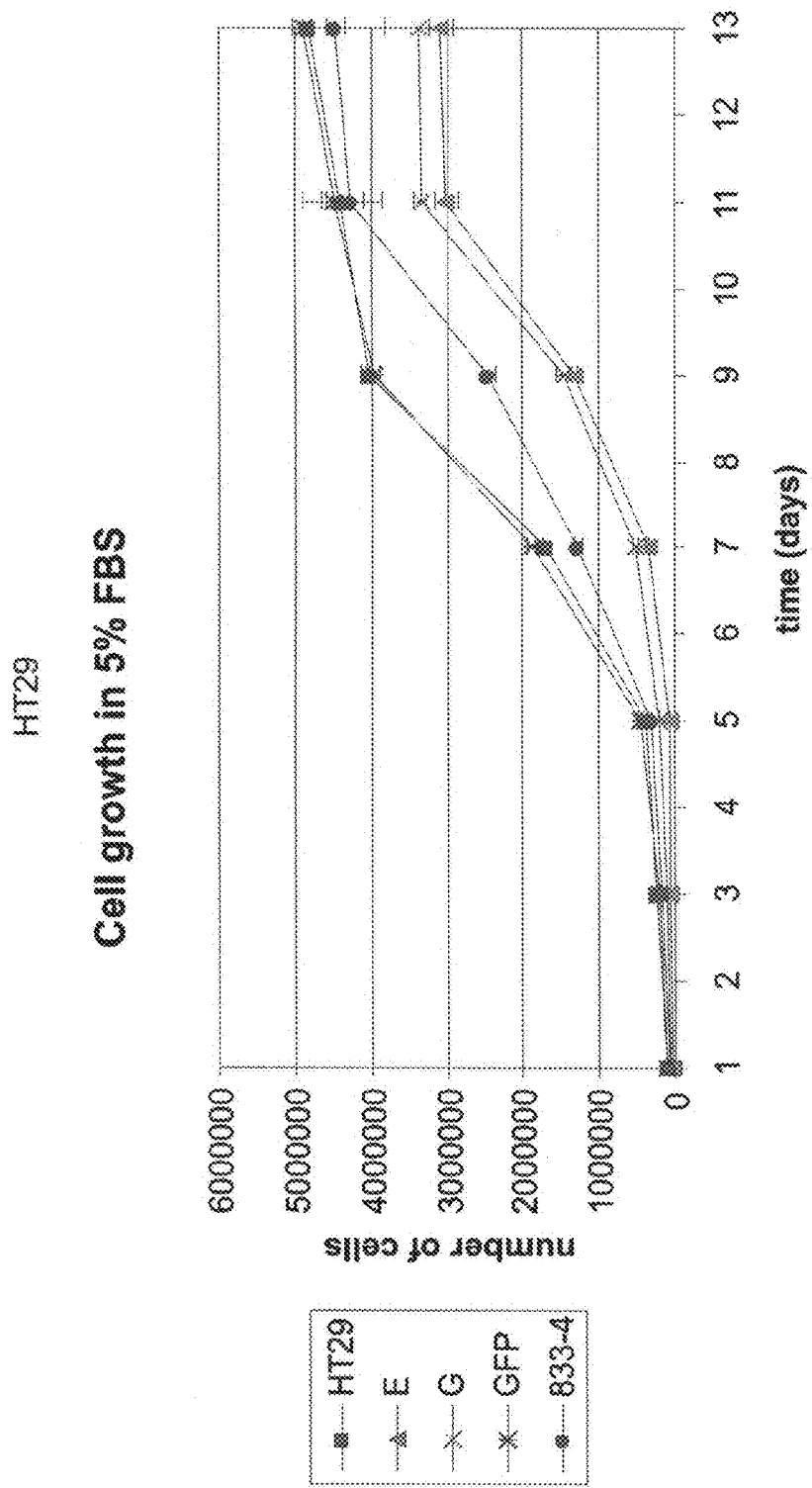
Figure 4B:
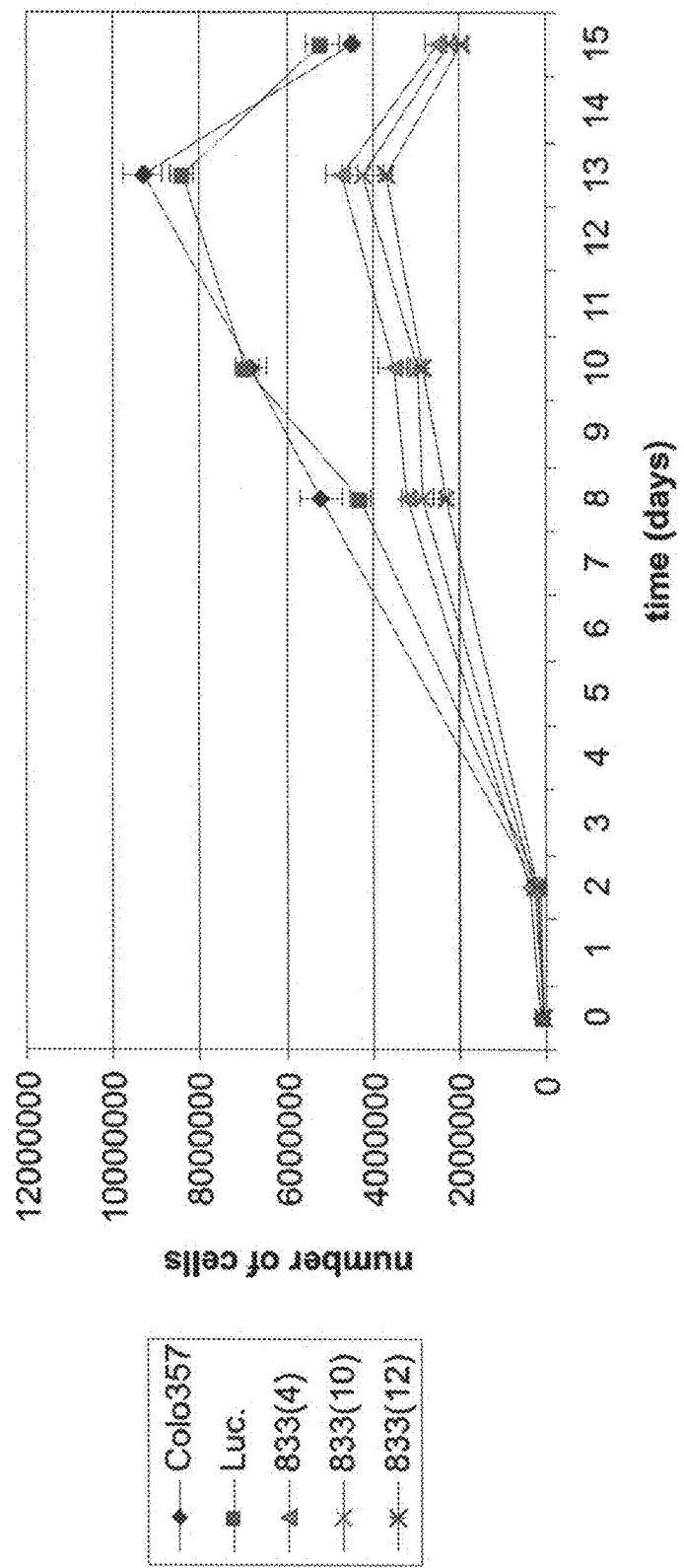
Figure 4C:
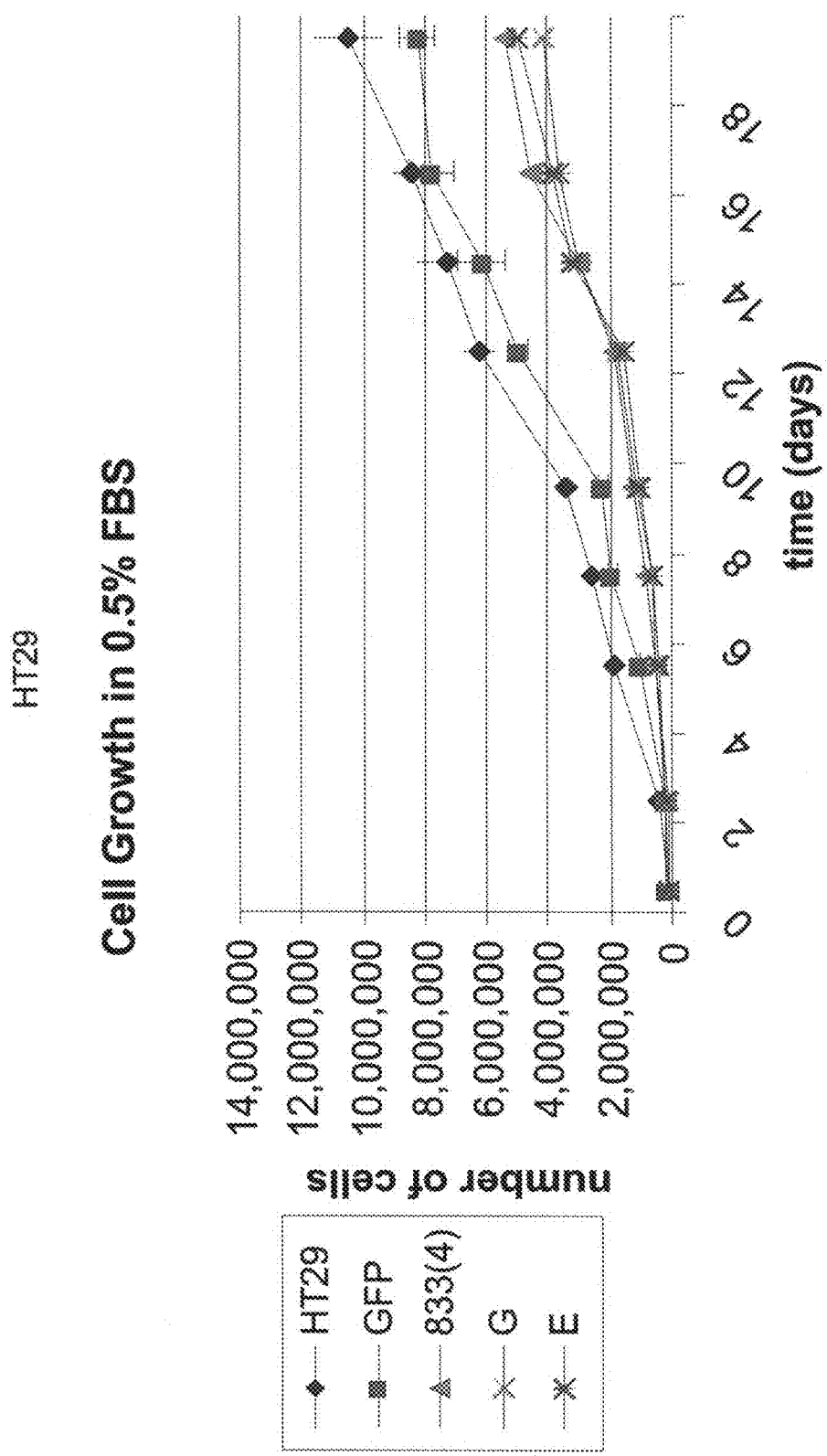
Figure 4D:
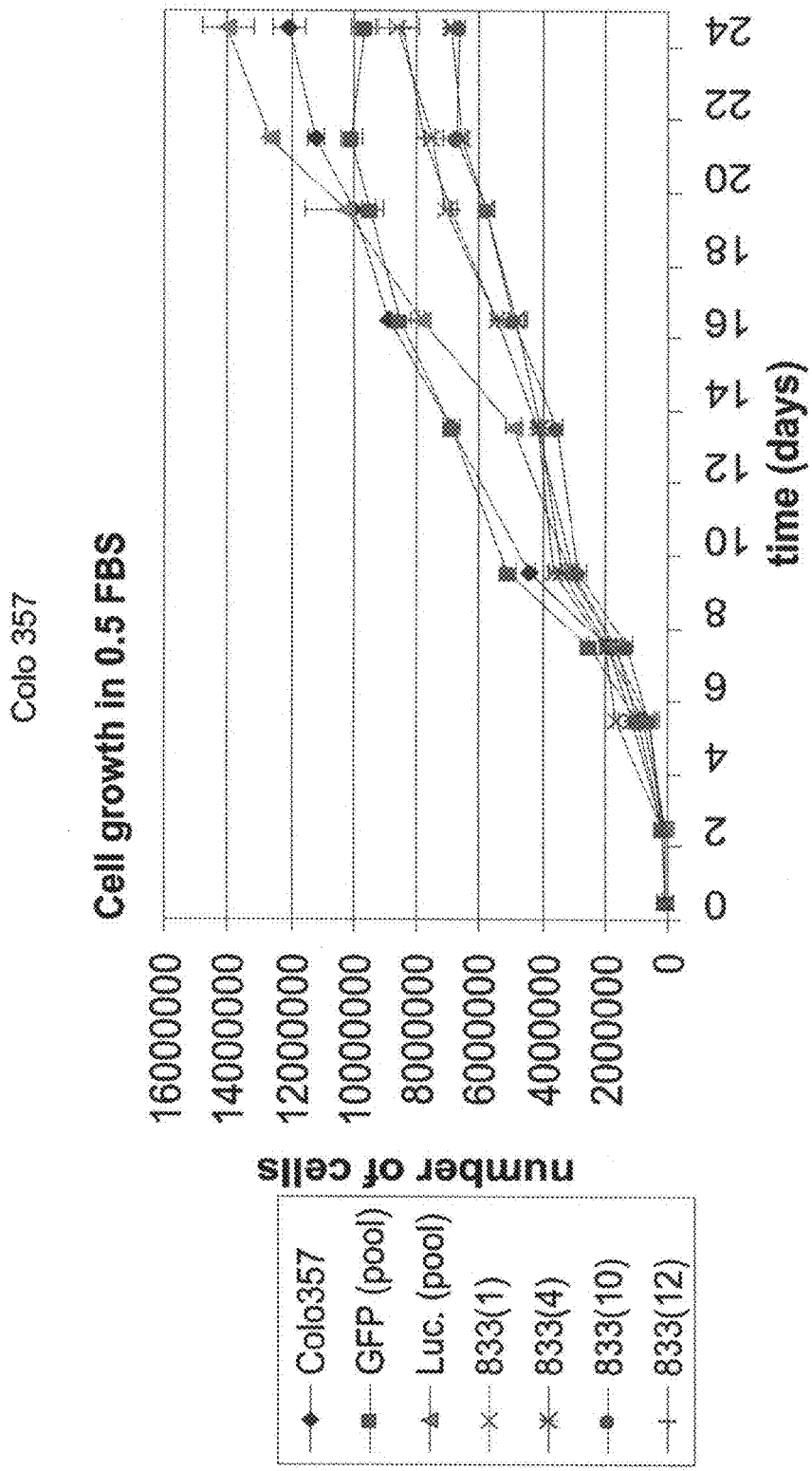

In order to improve the levels of reduction in the expression of the endogenous CD24, the most efficient HT29 clone was selected, which harbored the vector pSUPER-Puro-833, number 4, indicated with a star. This clone was transfected as described in Materials and Methods with the vector pSUPER-Hygro-1099 in order to produce clones where two different siRNA sequences to CD24 are simultaneously active. As a control, the same clone was transfected with pSUPER-Hygro-Luc as well. The clones that harbored both siRNA to CD24 at positions 833 and 1099 were numbered alphabetically by the order of their expansion (A to G). As illustrated in FIGS. 3A-C, Clones E and G showed a decrease in CD24 expression above 90% and were therefore chosen for further characterization, along with the parental HT29 cells, HT29 cells with control siRNA and the original single siRNA 833 (4) clone.

In order to validate the Western-blot analysis results and to analyze the level of surface CD24, flow cytometry analysis was performed to the different clones using anti-CD24 monoclonal antibody (ML-5) as the first binder and a fluorescent anti-Mouse antibody as the second binder. The results, illustrated in FIGS. 3D-E confirm the reduction in the CD24 expression levels.

Example 3

Down-Regulation of CD24 using siRNA Leads to CRC Cell Growth Inhibition in Culture Materials and Methods Measurement of cell proliferation: Cell proliferation and growth rate was measured to evaluate the change in doubling time and saturation densities of cells following CD24 overexpression: $3 \times 10^4$ cells per well from the parental cell, vector control and established clones were seeded in 12 well plates. For each cell, two wells were collected and counted every two days for two weeks. Results were repeated at least 3 times.

Results siRNA to CD24 was shown to reduce the growth rate of HT29 cells while control siRNA has no effect on the cells (FIGS. 4A-E). Clones E and G, derived from clone 833(4) with an additional siRNA to CD24 showed a significant decrease in growth rate.

Example 4

Down-Regulation of CD24 using siRNA Decreases Tumor Formation Rates in Nude-Mice Xenograft Model Materials and Methods Selected clones comprising control siRNA or the siRNAs of the present invention were injected into nude mice in order to check the level of their tumorigenicity in-vivo. In brief, exponentially growing cells were harvested with a brief treatment of 0.25% Trypsin EDTA solution and re-suspended at a final concentration of $7 \times 10^6$ cells per 0.15 ml per injection in PBS. Athymic nude mice were obtained and housed in sterile cages at the animal facilities in Tel Aviv Medical Center. Injecting the cells into two flanks of each animal produced subcutaneous tumors. Each tumor diameter was measured twice weekly using a micrometer caliper. Tumor volumes were calculated as: $4/3 * \pi r^3$. The radius was taken as the mean between longest and shortest measurement when tumors were not concentric.

Results

As illustrated in FIGS. 5A-B, clones that express low CD24 levels correlate with slower tumor formation (N=20). The results were similar for two experiments.

Example 5

Down-Regulation of CD24 Inhibits Migration in HT29 Cells

An important feature of malignant transformation is that the cell acquires the ability to detach from its original tissue and migrate through the basal membrane and invade deeper into regional tissues. The amoeboid movement and diapedesis depends on the ability to de- and re-construct actin filaments.

The following experiment was performed in order to analyse if down-regulation of CD24 effects migration in HT29 cells.

Materials and Methods

Migration Assay: A three-dimensional cell migration assay was performed with the Transwell system (Corning, N.Y.), which allows cells to migrate through an 8-µm pore size polycarbonate membrane. Complete medium was first added to the 24-well plate well (the lower chamber of Transwell), and then to the Transwell insert (the upper chamber of Transwell) and prepared in the incubator for 3-5 hours. Cells were trypsinized, washed and resuspended in DMEM medium containing 5% calf serum ($6 \times 10^5$ cells/ml). The cell suspension (100 µl) was plated onto the upper chamber of the Transwell. The lower chamber was filled with 600 µl of the same medium. After incubation for 48 hours at 37° C., the cells were fixed for 10 minutes in 4% paraformaldehyde, perforated with 0.01% Triton (Sigma) for 5 minutes and stained for 5 minutes with crystal violet. The filters were then rinsed thoroughly in distilled water and the non-migrating cells were carefully removed from the upper surface of the Transwell with a wet cotton swab. The wells were counted and the number of trans-migrated cells was assessed by color quantification using the TINA 2.0 software.

Results

Figure 6A:
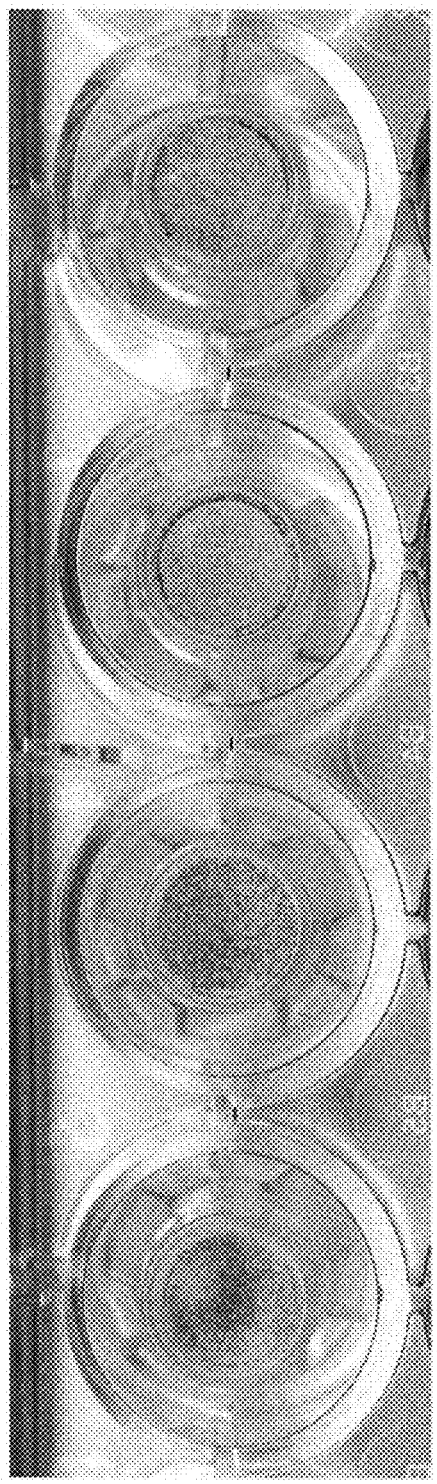
FIGS. 6A-B are photographs and graphs illustrating that HT29 cells in which the CD24 was down-regulated showed less migratory capacities, in proportion to the total cells number, in comparison to HT29 cells with control siRNA.
Figure 6B:
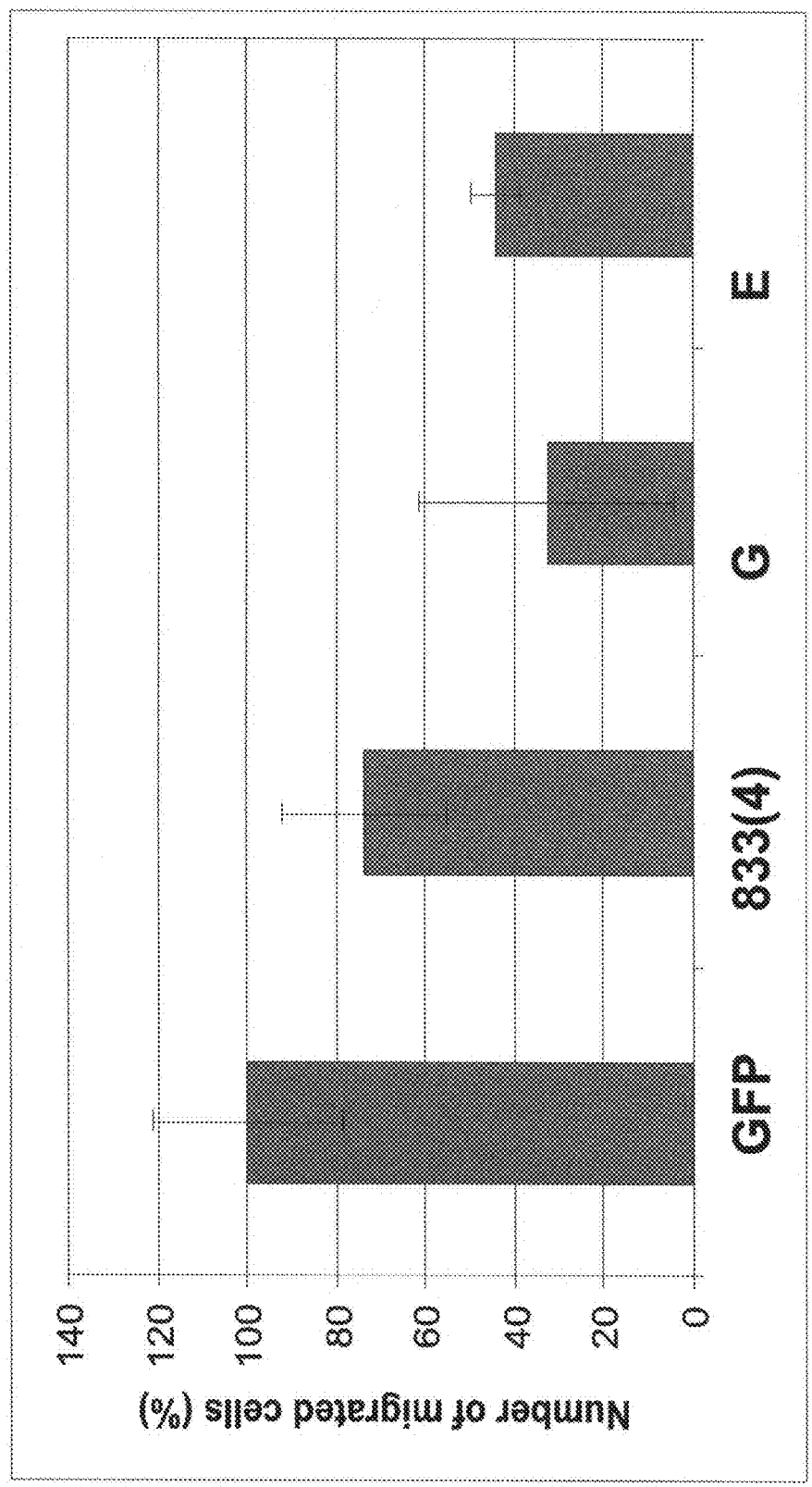

As illustrated in FIGS. 6A-B, cells in which the CD24 was down-regulated showed less migratory capacities and were fewer in numbers, in proportion to the total cells number, in comparison to HT29 cells with control siRNA. These results were repeated in three different trials.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An siRNA molecule selected from the group consisting of SEQ ID NO: 1, 3-4.

2. A method of treating a CD24-related medical condition, the method comprising administering to a subject in need thereof a therapeutically effective amount of at least one of said siRNA molecule of claim 1, thereby treating the CD24-related medical condition.

3. The method of claim 2, wherein the CD24-related medical condition is selected from the group consisting of a hyperproliferative disease and an autoimmune disease.

4. The method of claim 3, wherein said hyperproliferative disease is a colorectal cancer.

5. A pharmaceutical composition comprising at least one of said siRNA molecule of claim 1.

6. The pharmaceutical composition of claim 5, wherein said at least one of said siRNA molecule is two siRNA molecules set forth by SEQ ID NOs: 3 and 4.

7. An article of manufacture comprising two siRNA molecules set forth by SEQ ID NOs: 3 and 4.

* * * * *